United States Patent [19]

Glassman et al.

[11] 4,349,016

[45] Sep. 14, 1982

[54] LIVESTOCK SPLINT

[75] Inventors: Stephen M. Glassman; James D. Kia; Paul A. Ryding, all of Wichita, Kans.

[73] Assignee: KRG, Inc., Wichita, Kans.

[21] Appl. No.: 269,314

[22] Filed: Jun. 1, 1981

Related U.S. Application Data

[63] Continuation-in-part of Ser. No. 149,269, May 12, 1980, Pat. No. 4,320,722.

[51] Int. Cl.³ ............................................. A61F 5/04
[52] U.S. Cl. .................................. 128/87 R; 119/96
[58] Field of Search .................. 128/87 R, 89 R, 90, 128/83; 119/96, 127; 54/82

[56] References Cited

U.S. PATENT DOCUMENTS

| | | | |
|---|---|---|---|
| 765,354 | 6/1904 | Boone | 119/127 |
| 1,256,895 | 2/1918 | Handyside | 54/82 |
| 2,016,958 | 10/1935 | Clarke | 128/87 R X |
| 3,405,506 | 10/1968 | Kostur | 54/82 |
| 3,881,472 | 5/1975 | Lee | 119/96 X |

Primary Examiner—John D. Yasko
Attorney, Agent, or Firm—John H. Widdowson

[57] ABSTRACT

An animal brace having a shell member; a foam padding connected to the inside of the shell; and a reinforced back connected to and traversing the back of the shell member.

10 Claims, 7 Drawing Figures

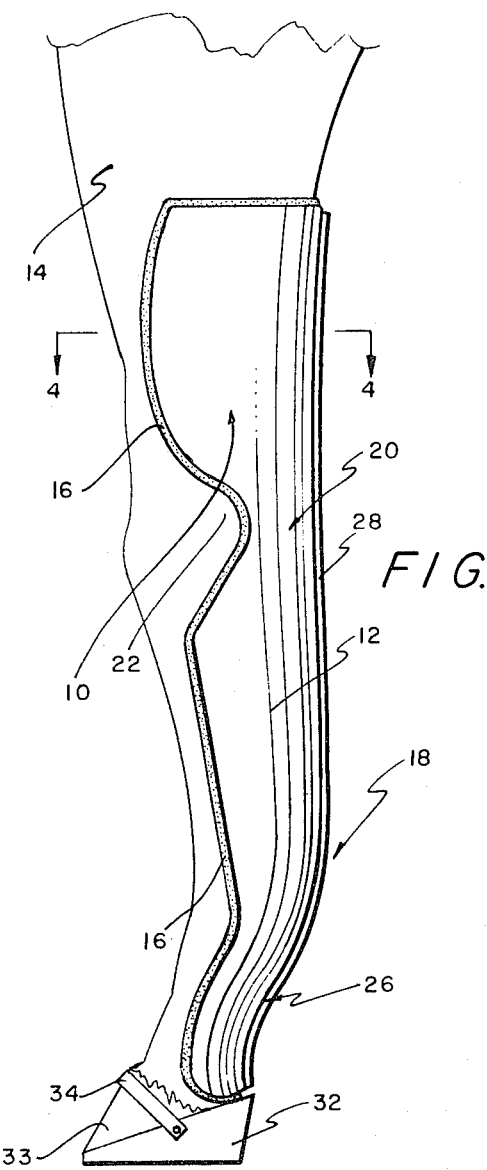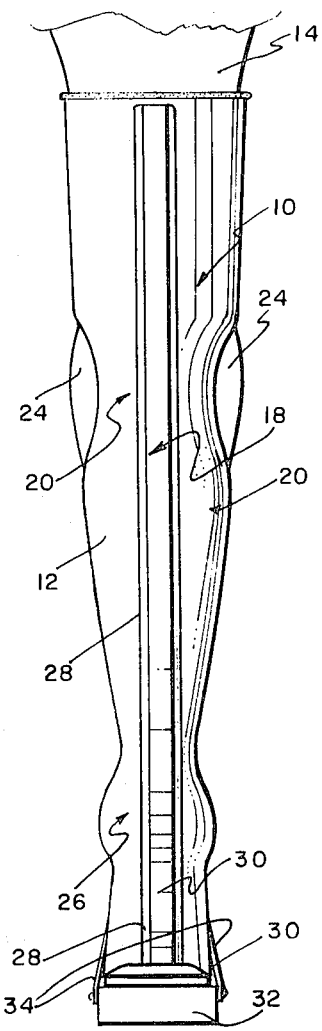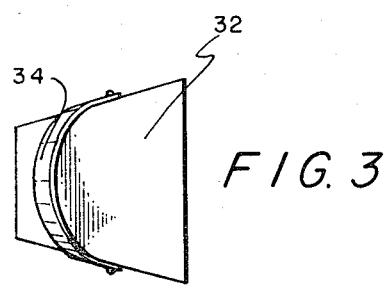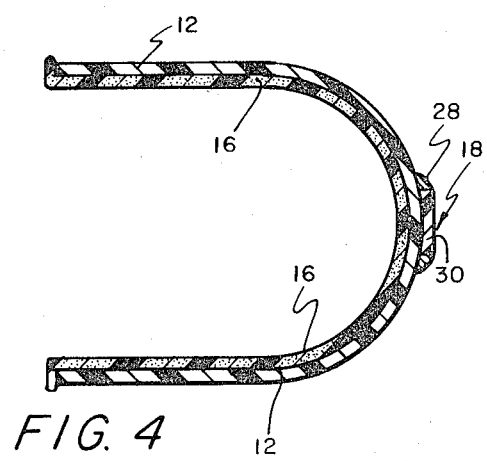

4,349,016

LIVESTOCK SPLINT

BACKGROUND OF THE INVENTION

This is a continuation-in-part application of our co-pending application Ser. No. 149,269 filed May 12, 1980 now U.S. Pat. No. 4,320,722.

FIELD OF THE INVENTION

This invention is related to an animal brace. More specifically this invention provides an equine animal splint which may be placed on the front leg of the animal.

DESCRIPTION OF THE PRIOR ART

Historically, veterinarians and laymen have designed and constructed a variety of braces and fixation devices. Two common problems have been consistent with these devices. First, the units are too heavy and cumbersome. Second, they fail to adequately support the injured leg, primarily due to the difficultly in applying the device without other support items.

U.S. Pat. No. 4,029,090 describes an apparatus designed to be used with casting material with the intent of adding to the support of the leg. U.S. Pat. No. 4,044,760 shows a small plastic device with the intended purpose of supporting the flexor tendons. U.S. Pat. No. 4,099,525 describes a device using cast material in an attempt to stretch contracted tendons.

SUMMARY OF THE INVENTION

This invention accomplishes its desired objects by providing an animal leg brace or splint which is comprised of a shell member with sides for partially encasing the leg of the animal and which fits behind the leg of the animal. A foam padding means connects to the inside of the shell member to protect the leg of the animal. A reinforced back means connects to and traverses the back of the shell member to prevent the animal from fatiguing the brace prematurely. The shell member has a carpal section on each of said sides for contiguously resting in proximity to the carpal area of the leg of the animal.

It is an object of the invention to provide a leg brace which is easily assembled and economical to manufacture.

Still further objects of the invention reside in the provision of an animal brace which can be easily attached to the leg of an animal.

These, together with the various ancillary objects and features which will become apparent as the following description proceeds, are attained by this animal brace, preferred embodiments being shown in the accompanying drawings, by way of example only, wherein;

BRIEF DESCRIPTION OF THE DRAWINGS

FIG. 1 is a side elevational view of the leg brace around the leg of an animal with the toe wedge strapped to the hoof;

FIG. 2 is a rear elevational view of the leg brace disclosing the reinforced rectangular strip and the back of the toe wedge;

FIG. 3 is a top plan view of the toe wedge and the metal strap;

FIG. 4 is a horizontal sectional view taken in direction of the arrows and along the plane of line 4—4 in FIG. 1;

DETAILED DESCRIPTION OF THE DRAWINGS

Figure 5:
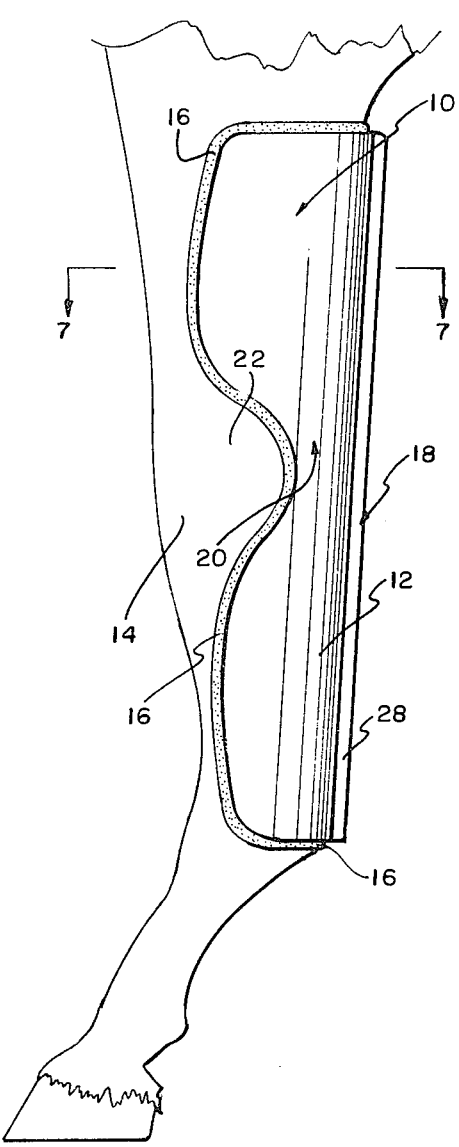
FIG. 5 is a side elevational view of another embodiment of the leg brace around the leg of an animal.
Figure 6:
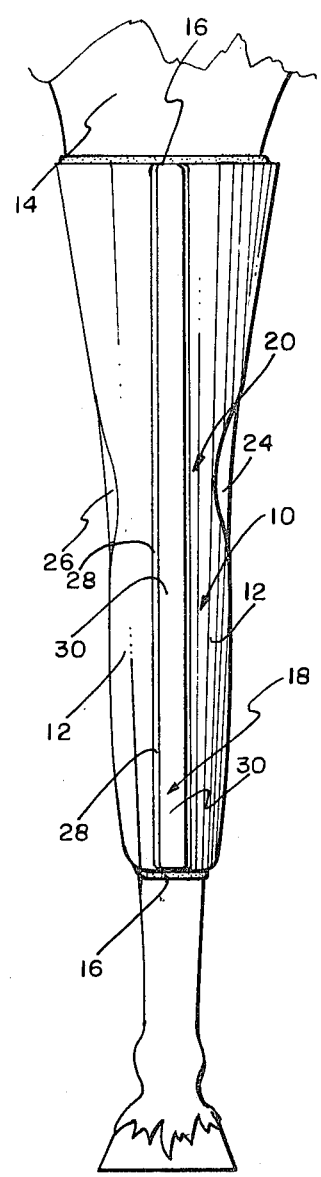
FIG. 6 is a rear elevational view of the leg brace of FIG. 5 disclosing the reinforced rectangular strip.
Figure 7:
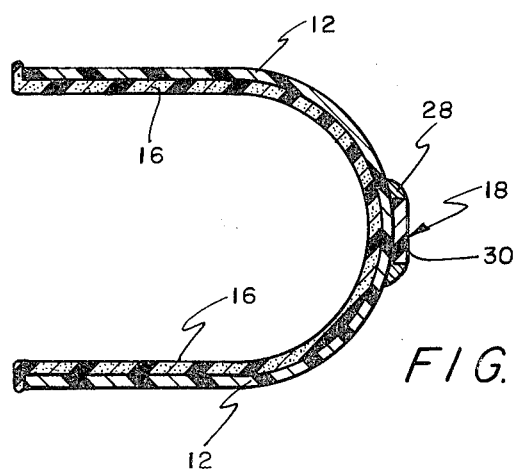
FIG. 7 is a horizontal sectional view taken in direction of the arrows and along the plane of line 7—7 in FIG. 5.

Referring in detail now to the drawings, wherein like reference numerals designate similar parts throughout the various views, a fiberglass reinforced plastic shell, generally illustrated as 10, having sides 12—12 for partially encasing a leg 14 of an animal (not shown in the drawings). A foam padding means 16 connects to the inside of the shell 10 to protect the leg 14 of the animal from pressure sores and insures a proper therapeutic fit. A reinforced back means, generally illustrated as 18, connects to and traverses the back of the shell 10 to prevent the animal from fatiguing the brace or splint of this invention. The shell member 10 has a carpal section, generally illustrated as 20, on each side 12—12 for contiguously resting in proximity to the carpal area of the leg 14 of the animal. The carpal section 20 of each of the sides 12—12, as evidenced in the drawings, has a structure generally defined as the residual structure remaining after an essentially U-shaped section 22 (see FIGS. 1 and 5) is removed from a section of the sides 12—12 of the shell member 10 to accomodate the joint 24 in the carpal area of the leg 14 of the animal such that further injury to the leg 14 of the animal is not incurred.

In the animal front leg 14 embodiment of the invention in FIGS. 1-4, the shell 10 additionally includes a fetlock-pastern section, generally illustrated as 26 (see FIGS. 1 and 2), which also includes foam padding means 16 attached therein and reinforced back means 18 connected to and traversing the back thereof. The fetlock-pastern section 26 is defined by a bulge in the sides 12—12 of shell 10 as illustrated in FIG. 2. The reinforced back means 18 also prevents the animal fatiguing the fetlock-pastern section 26 in addition to the carpal section 20 of the shell 10.

The reinforced back means 18 comprises a generally rectangular strip 28 of a 2415 woven rowing mat means (known to those possessing ordinary skill in the art of plastics and the like) placed on top of a strip of plain weave volan finish down the back of the shell 10. Superimposed on top of the 2415 woven rowing mat means strip 28 is a strip 30 of a core mat means imported from Holland (by West Point Pepperell) and also known to those in the plastic industry. On top of the core mat strip 30 is placed a rectangular layer of volan finish glass gabric means which is yet further well known in the plastic business.

A generally triangular in vertical cross section toe wedge means 32, also in the front leg 14 embodiment of FIGS. 1-7, supports a hoof 33 of the animal. A metal band means 34 connects to the wedge 32 for rising over the top of the hoof 33. The wedge means 32 may be attahced to the hoof 33 by glue or nails as disclosed in our co-pending application. The toe wedge 32 may be constructed of a synthetic rubber means (e.g. neoprene) such that when the hoof 33 of the animal is glued or nailed to the wedge 32, the excess synthetic rubber means surrounding the outside of the hoof 33 is capable of being trimmed away.

With continuing reference to the drawings for operation of the invention, the leg 14 (front leg in FIGS. 1-7) of the animal is placed in the rubber padded shell 10 with the front hoof 33 situated on the wedge 32. The metal band 34 is raised over the hoof 33, or the synthetic rubber wedge 32 is nailed or glued to the hoof 33 and the excess wedge may be trimmed away. Any popular self-adhering wrap or tape may hold the shell 10 around the leg 14. All that is needed to remove the shell 10 is a pair of scissors to cut the wrap or tape. The toe wedge 32 is removed with either a screwdriver, a horseshoe hammer, or a sharp knife, depending on choice of application.

While the present invention has been described herein with reference to particular embodiments thereof, a latitude of modification, various changes and substitutes are intended in the foregoing disclosure, and it will be appreciated that in some instances some features of the invention will be employed without a corresponding use of other features without departing from the scope of the invention as set forth.

We claim:

1. An animal leg brace or splint which is comprised of a shell member with sides for partially encasing the leg of the animal, and which fits behind the leg of the animal; a foam padding means connected to the inside of said shell member to protect the leg of the animal from pressure sores and insure a proper therapeutic fit; a reinforced back means connected to and traversing the back of said shell member to prevent the animal from fatiguing the brace or splint prematurely; said shell member having a carpal section on each of said sides for contiguously resting in proximity to the carpal area of the leg of the animal, said carpal section of each of said sides having a structure generally defined by the residual structure after an essentially U-shaped section is removed from a section of said sides of said shell member to accomodate the joint in the carpal area of the leg of the animal such that further injury to the forelimb of the animal is not incurred.

2. The brace of claim 1 wherein said shell member additionally comprises a fetlock-pastern section for partially enclosing the fetlock and pastern joint of the animal to contract the forelimb back for therapeutic reasons.

3. The brace of claim 1 wherein said fetlock-pastern section of said shell member additionally includes said foam padding means connected to the inside thereof and said reinforced back means connected to and traversing the back of said fetlock-pastern section to prevent the animal from fatiguing the carpal section and the fetlock-pastern section of the shell member.

4. The brace of claim 3 wherein said fetlock-pastern section of said shell member is defined by a bulge in the sides thereof.

5. The brace of claim 4 wherein said reinforced back means comprises a generally rectangular strip of a woven rowing mat means, and a rectangular strip of core mat means superimposed on said rowing mat.

6. The brace of claim 5 wherein said reinforced back means additionally comprises a rectangular glass fabric means layered on top of said core mat means.

7. The brace of claim 6 additionally comprising a toe wedge means for supporting the hoof of the animal, a metal band means connected to the toe wedge for rising over the top of the hoof of the animal.

8. The brace of claim 6 additionally comprising a toe wedge means for supporting the hoof of the animal, said toe wedge means is constructed of a synthetic rubber means so that when the hoof of the animal is glued or nailed to the wedge means, the excess synthetic rubber means surrounding the outside of the hoof is capable of being trimmed away.

9. The brace of claim 7 wherein said toe wedge means is essentially triangular in a vertical cross section.

10. The brace of claim 8 wherein said toe wedge means is essentially triangular in a vertical cross section.

* * * * *